United States Patent [19]

Eloy

[11] Patent Number: 5,760,362

[45] Date of Patent: Jun. 2, 1998

[54] APPARATUS FOR TREATING A MATERIAL HAVING A MINIATURIZED PHOTOIONIC HEAD

[75] Inventor: Jean-François Eloy, Gradignan, France

[73] Assignee: Commissariat A L'Energie Atomique, Paris, France

[21] Appl. No.: 605,054

[22] PCT Filed: Sep. 7, 1994

[86] PCT No.: PCT/FR94/01054

§ 371 Date: Mar. 1, 1996

§ 102(e) Date: Mar. 1, 1996

[87] PCT Pub. No.: WO95/07368

PCT Pub. Date: Mar. 16, 1995

[30] Foreign Application Priority Data

Sep. 8, 1993 [FR] France ................ 93/10657

[51] Int. Cl.⁶ .......................... B23K 26/00; C23C 14/04
[52] U.S. Cl. .......................... 219/121.6; 219/121.83; 118/623
[58] Field of Search .......................... 219/121.6, 121.73, 219/121.78, 121.83, 121.84, 121.85, 121.76; 606/15, 16; 385/33, 39, 88, 134; 118/620, 623, 621; 372/70; 427/555, 596

[56] References Cited

U.S. PATENT DOCUMENTS

| | | | |
|---|---|---|---|
| 3,622,743 | 11/1971 | Muncheryan | 219/121.63 |
| 3,947,088 | 3/1976 | French | 385/31 |
| 4,170,997 | 10/1979 | Pinnow et al. | 606/15 X |
| 4,388,924 | 6/1983 | Weissman et al. | 606/16 |
| 4,538,609 | 9/1985 | Takenaka et al. | 606/16 |
| 4,686,979 | 8/1987 | Gruen et al. | 606/15 X |
| 4,714,628 | 12/1987 | Eloy . | |
| 4,752,455 | 6/1988 | Mayer . | |
| 4,778,693 | 10/1988 | Drozdowicz et al. . | |
| 4,843,209 | 6/1989 | Milligan | 219/121.73 X |
| 4,860,172 | 8/1989 | Schlager et al. | 606/16 X |
| 5,150,704 | 9/1992 | Tatebayashi et al. | 607/89 |

FOREIGN PATENT DOCUMENTS

| | | |
|---|---|---|
| 0 239 432 A1 | 9/1987 | European Pat. Off. . |
| 0 546 921 A1 | 6/1993 | European Pat. Off. . |
| 2.083.740 | 12/1971 | France . |
| 2 623 820 | 6/1989 | France . |
| 25 23 982 | 12/1976 | Germany . |
| 54-108094 | 8/1979 | Japan ............... 219/121.73 |
| 1-104492 | 4/1989 | Japan ............... 219/121.75 |

Primary Examiner—Gregory L. Mills
Attorney, Agent, or Firm—Burns, Doane, Swecker & Mathis, LLP

[57] ABSTRACT

Apparatus for treating a material having a miniaturized photoionic head including at least one optical fiber (2), a pulsed light source permitting the treatment of the material (10), a light injector for injecting light into one end of the fiber and a miniaturized photoionic head (8) having a ring (16). One side of the ring is fixed to the other end of the fiber, and the other side of the ring is against the material. This ring confines a plasma forming, due to the pulsed light, in the space defined by the ring, from a material or a substance (20) placed in the space, for the treatment of the material such as surface treatment of metals.

18 Claims, 4 Drawing Sheets

APPARATUS FOR TREATING A MATERIAL HAVING A MINIATURIZED PHOTOIONIC HEAD

BACKGROUND OF THE INVENTION

The present invention relates to an apparatus for treating a material having a miniaturized photoionic head.

Over a wide variety of surfaces of objects having very small sizes and which are difficult of access, it permits the performance of the following micro-localized treatments:

platings, sealing cracks, surface hardening, production of new alloys, production of superalloys.

It more particularly applies:

in dental surgery to the localized treatment of teeth (cracks, caries and prostheses in situ on a patient), in order to bring about a reinforcement of the enamel and the resistance to caries, to microelectronics (localized deposition of specific coatings, restoration or destroying of functions of components of a microcircuit, producing new types of alloys for electrical connections), to micromechanics (surface hardening of inexpensive alloys for clock and watch-making), to localized automatic treatment in a chemically aggressive or radioactive atmosphere, to the localized automatic treatment in a liquid medium and in particular a submarine medium.

It is known that the ionic implantation of certain chemical species in the surface layer of certain alloys modifies the surface mechanical properties thereof (resistance to wear, friction, sand abrasion, corrosion, etc.).

Moreover, it is known that among the effects induced by the impact of a laser beam on a solid material, there is the appearance of an ionized vapour and frequently a plasma which, by their expansion effects, induce a recoil wave which can itself lead to a surface hardening of the material from which said vapour and said plasma have come.

It is also known that the impact of a laser beam on a surface layer deposited on a transparent support can induce, by transmitting the laser beam through said support, the evaporation of the deposited layer which can therefore be subsequently condensed on another support.

It is also known that the deposition of a thin film by cathodic sputtering can be assisted by the impact of a laser beam on the film during condensation and growth.

This has the consequence of improving the deposited film qualities (cohesion, adhesion, dielectric properties).

Reference should be made in this connection to:

(1) French patent application application 8306749 of 25 Apr. 1983, Process for Amorphous Growth of a Material with Crystallization under Radiation, André Chenevas-Paule, Robert Cuchet and Jean-François Eloy, cf. also EP-A-127499 and U.S. Pat. No. 4,529,617.

It is also known that the combination or coupling of several effects (such as explosive evaporation, ionic implantation induced by an electric potential difference for separating electronic and ionic charges, the thermal wave induced by the condensation of the ionic plasma, the ultra-fast hardening induced by the heat well represented by the thermal capacitance of the material receiving said ionic plasma) rendered simultaneous by the use of a high power, pulsed laser beam, can give rise to material surface layers having novel mechanical and physicochemical properties able to improve their use (resistance to wear, friction, sand abrasion, corrosion, etc.).

Reference can be made in this connection to:

(2) French patent application 8602568 of 25 Feb. 1986, Process and Apparatus for Treating a Material by a Thermoionic Effect with a View to Modifying its Physicochemical Properties, Jean-François Eloy, cf. also EP-A-239432 and U.S. Pat. No. 4,714,628.

The known shockwave surface treatment apparatuses do not make it possible to take advantage of the aforementioned processes and phenomena for all surface forms or parts to be treated.

Thus, the known apparatuses are cumbersome, particularly with regards to that described in document (2), the linear propagation of the laser beam used therein requiring:

a direct vision of the surface to be treated and a direct access of the laser beam to said surface to be treated, a transparent window serving on the one hand as the fixed and rigid material source for the shockwave and on the other as a reference surface fixing the propagation direction of said shockwave (which is induced by the evaporation due to the laser) towards the material to be treated, an electrically insulating ring permitting the confinement of the pressure wave of the ionized plasma so as to guide it in the direction of the surface to be treated, said insulating ring also serving as a spacer separating the layer to be exploded from the surface to be treated.

These different elements of the apparatus described in document (2) limit the application thereof to planar or possibly slightly inwardly curved surfaces.

Moreover, the geometrical characteristics of the laser beam used in said apparatus limit the specific treatments which can be carried out with said apparatus to wide surfaces to which relatively easy and direct access are possible.

For other surfaces, these characteristics of the laser beam require the development of sophisticated optical systems specific to each geometrical shape of the part to be treated.

The apparatus described in (2) does not permit the treatment of surfaces having random shapes and in particular small surfaces located in areas of a part or a complex shaped device, which only permit the treatment of a restricted space and to which linear access is not possible.

The present invention aims at obviating the aforementioned disadvantages by proposing an apparatus for the treatment of a material with the aid of an intense light beam and at least one optical fibre for transporting the latter.

This optical fibre, provided with a miniaturized photoionic head (i.e. whose transverse dimensions only slightly exceed by approximately 20% those of the optical fibre) enable said beam to be guided and have access to any surface, with reduced dimensions and with geometrically restricted access, of a part having a random shape and structure.

In certain embodiments, the apparatus according to the invention permits a putting into place, in a simplified and programmable manner in space, one or more miniaturized photoionic heads, with a view to a laser-assisted treatment and in particular an ionic implantation.

More specifically, the present invention relates to an apparatus for the treatment of a material, characterized in that it comprises:

at least one optical fibre, a first light source for producing a pulsed light permitting the treatment of the material, a means for injecting said pulsed light into a first end of each optical fibre and for each optical fibre, a miniaturized photoionic head incorporating a confinement ring, whereof a first side is joined to the second end of the fibre, whereas the second side of the ring is to be placed against the material, said ring being able to confine a plasma which can form, due to the pulsed light, in the space defined by said ring, from the material or substance placed in said space, with a view to the treatment of the material.

The miniaturized photoionic head or heads of the apparatus according to the invention permit, according to the known apparatus described in document (2), a localized surface hardening of a material, but the apparatus according to the invention has much smaller overall dimensions than the known apparatus, due to the fact that it uses one or more miniaturized photoionic heads.

According to an embodiment of the apparatus according to the invention, the confinement ring is electrically insulating, each optical fibre being coated with an electrically conductive sheath, the material placed in the space defined by the confinement ring forms a solid thin film placed against the second end of the optical fibre and at a distance from the material and which is to be transformed, by means of the pulsed light, into a plasma containing ions, and the apparatus also comprises a means for polarizing the electrically conductive sheath with respect to the material in order to create, in the space defined by the confinement ring, an electrical field able to accelerate the ions of the plasma towards the material with a view to implanting them therein.

The material forming the solid thin film can be electrically conductive or semiconducting. This material can also be electrically insulating and in this case the apparatus according to the invention also comprises a ring, which is electrically conductive and connected to the conductive sheath and which is positioned substantially level with the thin film against the outer wall of the confinement ring.

In an embodiment, the apparatus according to the invention also comprises a lens, which is optically coupled to the second end of the optical fibre and which has a convex face in the space defined by the confinement ring, said face is to be located on the side of the material to be treated and the thin film is formed on said convex face.

In another special embodiment, the second end of the optical fibre has a convex portion in the space defined by the confinement ring and the thin film is formed on said convex portion.

In another special embodiment, the apparatus according to the invention also comprises a pellet, which is transparent to the pulsed light, which is optically coupled to the second end of the optical fibre and placed in the space defined by the confinement ring and whose face to be located on the side of the material to be treated carries the thin film.

In another special embodiment, the apparatus also comprises a strip on which is formed the thin film and a means for moving said strip between the second end of the optical fibre and the confinement ring.

The apparatus according to the invention can also comprise an intermediate layer between the fibre and the thin film, said intermediate layer being provided for adapting the optical index of the fibre to that of the thin film, so as to reduce the pulsed light quantity which can be reflected by said thin film.

According to another embodiment of the invention, the apparatus also comprises, in the space defined by the confinement ring, a fluid filling said space and transparent to the pulsed light, so as to harden the material by the confinement of the plasma formed by the interaction of the pulsed light with said material, or which is photodecomposable and photoionizable by said pulsed light, so as to chemically treat the surface of the material by chemical species produced during the photoionization and photodecomposition process.

The first light source can be a pulsed power laser.

As a variant, the first light source is a power source of pulsed, incoherent light and the apparatus also comprises a laser diode optically coupled to the second end of the optical fibre and able to produce a power, pulsed laser beam when it receives the pulsed light from the first source.

In an embodiment of the apparatus according to the invention, the optical fibre comprises:

a central optical fibre for transmitting the pulsed light and an annular optical fibre surrounding the central optical fibre, and the apparatus also comprises:

a second light source for producing a visible light permitting the observation of the material, a means for injecting said observation light into the annular optical fibre and a means for displaying the image of the material, from the observation light reflected by the material and transmitted by the annular optical fibre.

The apparatus according to the invention can also comprise a means for positioning the optical head facing a selected area of the material.

The apparatus according to the invention may comprise a plurality of optical fibres respectively associated with a plurality of photoionic heads, in order to simultaneously treat a plurality of material areas.

BRIEF DESCRIPTION OF THE DRAWINGS

The invention is described in greater detail hereinafter relative to non-limitative embodiments and the attached drawings, wherein show.

DETAILED DESCRIPTION OF THE INVENTION

Figure 1:
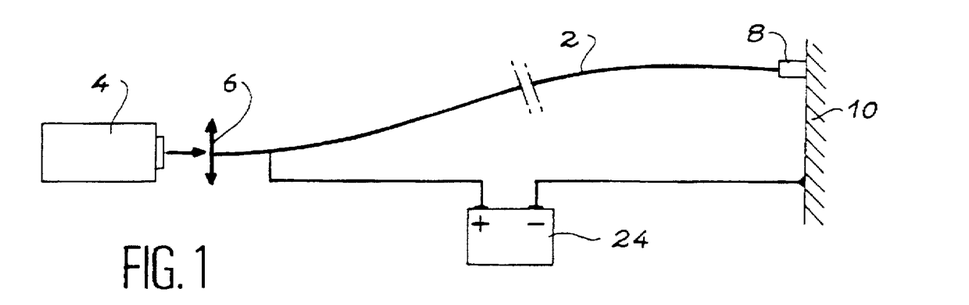
FIG. 1 A diagrammatic view of an embodiment of the apparatus according to the invention.

The treatment apparatus according to the invention, which is diagrammatically shown in FIG. 1 comprises an optical fibre 2, a power laser 4 able to emit a pulsed laser beam, a means 6 for injecting said laser beam into one of the two ends of the optical fibre 2 and a miniaturized photoionic head 8 fitted at the other end of the fibre 2.

Figure 2:
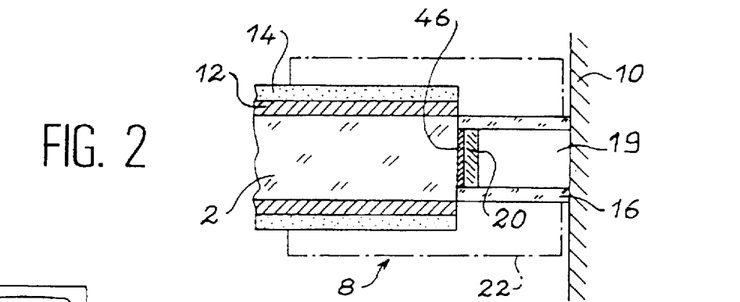
FIG. 2 A diagrammatic view of the miniaturized photoionic head of the apparatus of FIG. 1.

This miniaturized photoionic head 8, which permits the treatment of a material 10, is diagrammatically shown in FIG. 2. Neither the core, nor the optical sheath of the fibre 2 are shown. The face of the end of said fibre in which is fitted the head 8 is planar.

It can be seen that the fibre 2 has an electrically conductive sheath 12 (e.g. a braided metal sheath) surrounding the optical sheath of the fibre over the entire length of the latter, as well as another electrically insulating sheath 14 surrounding the sheath 12 and which serves as a protective sheath.

The head 8 comprises an electrically insulating ring 16, whose external diameter is substantially equal to the external diameter of the optical sheath of the fibre and which is placed, on one side, against the planar face of the end of said fibre, whereas the other side of the ring 16 is to be placed against the material 10 to be treated. More specifically, the head 8 is positioned in such a way that the ring 16 surrounds an area 18 of the material to be treated.

The head 8 also comprises a thin film 20 made from a material which it is wished to project, as will be shown hereinafter, by a shockwave in the direction of the area 18 to be treated. This thin film 20 is placed in the space defined by the ring 16, against the planar face of the end of the fibre 2 and is consequently spaced from the area 18 to be treated.

An electrically insulating part 22, whose transverse dimensions (considered perpendicular to the axis of the end of the optical fibre) only exceed slightly by approximately 20% the diameter of the sheath 14, is intended to rigidly join together the ring 16 containing the thin film 20 and the end of the fibre 2.

The apparatus of FIGS. 1 and 2 also comprises a means 24 making it possible to positively polarize in an time-constant manner, the conductive sheath 12 with respect to the material 10 to be treated, the latter being earthed.

This polarization is chosen so as to be able to establish, in the space defined by the sheath 16, an electric field able to accelerate ions formed from the thin film 20, as will be described hereinafter, with a view to the implantation of these ions in area 18 of material 10. To implant the ions in area 18 of the material, in front of which is located the thin film 20, the following procedure is adopted.

The laser 4 is initiated and then emits a power light pulse, which is injected into the fibre 2, where it propagates up to the photoionic head 8. This power pulse reaches the thin film 20 and brings about the explosive evaporation thereof.

A plasma forms in the space 19 defined by the ring 16 and the positive ions of said plasma are accelerated in the direction of the area 18 by the electric field established in the manner indicated hereinbefore. They are then implanted in said area 18 (whilst the electrons of the plasma are accelerated in the opposite direction towards the fibre 2).

The ring 16 is used for confining the plasma and the explosive wave produced during the formation thereof, to the space 19 and therefore to the area 18.

Figure 3:
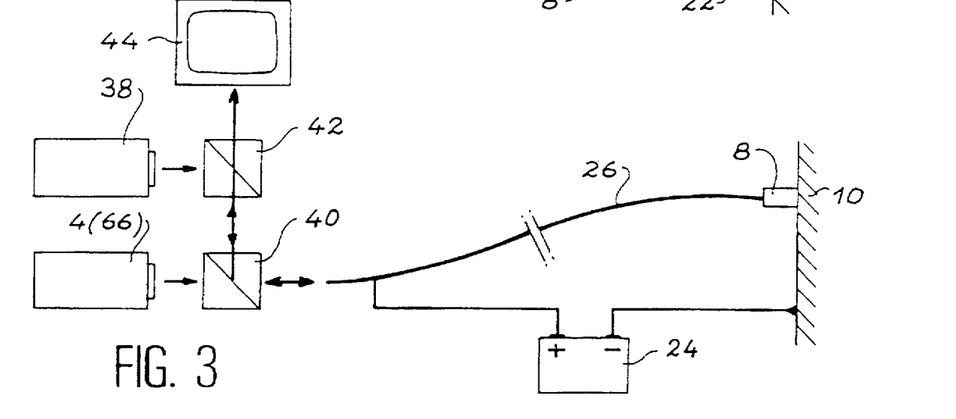
FIG. 3 A diagrammatic view of another embodiment of the apparatus according to the invention, provided with means for observing the material to be treated.

The apparatus according to the invention and which is diagrammatically shown in FIG. 3 permits the observation of the area which it is wished to treat and therefore a correct positioning of the photoionic head facing said area and then, following the treatment of said area, permits an observation of the treated area.

The apparatus of FIG. 3 comprises an optical fibre 26, whereof one end is provided with a photoionic head 8. The fibre 26 is a double optical fibre having a central optical fibre 30 and an annular optical fibre 32 surrounding the fibre 30 and as can be seen in FIG. 4.

The fibre 26 also comprises the conductive sheath 12 which, in the present case, surrounds the annular fibre 32, as well as the electrically insulating, protective sheath 14 surrounding the sheath 12.

Figure 4:
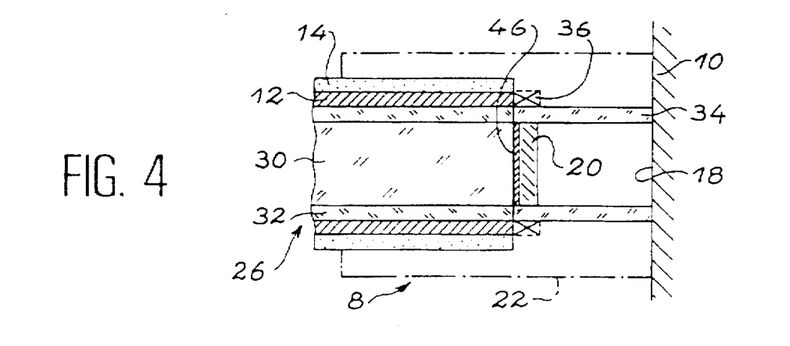
FIG. 4 A diagrammatic view of the miniaturized photoionic head of the apparatus of FIG. 3.

In the apparatus of FIG. 3, the photoionic head also comprises an electrically insulating ring 34, whose internal diameter and external diameter substantially correspond respectively to the internal and external diameters of the annular fibre 32, as can be seen in FIG. 4.

The ring 34 is made from a material transparent to the light liable to propagate in the annular fibre 32 and rests against the planar face of the end of the fibre 26, coinciding with the annular fibres 32 in order to form an optical extension thereof, as shown in FIG. 4.

The photoionic head of FIG. 4 also comprises the thin film 20 which, in the case of FIG. 4, rests against the planar face of the end of the central fibre 30, in the space defined by the ring 34 and therefore at a distance from the area 18 of the material 10 to be treated.

The apparatus of FIG. 3 also comprises the means 24 for the constant polarization of the conductive sheath 12 with respect to the material 10 in order to establish the aforementioned electrical field in the space defined by the confinement ring 34. The film 20 can be made from an electrically conducting or semiconductive material.

However, said film 20 can also be made from an electrically insulating material but, in this case, to the photoionic head 8 is added a small electrically conductive ring 36, which is electrically connected to the sheath 12 and surrounds the confinement ring 34, substantially level with said insulating film 20 and as shown in FIG. 4.

Apart from the pulsed power laser 4, the apparatus of FIG. 3 comprises another laser 38 able to continuously emit visible light for the observation of the area to be treated.

A device 40 is provided for the coupling and optical injection of the pulsed power laser beam emitted by the laser 4 into the fibre 26.

A second optical device 42 is provided for the coupling and injection of the continuous observation laser beam emitted by the laser 38 into said fibre 26.

In the represented embodiment, the devices 40 and 42 incorporate separating optics, the light from the optics 42 passing through the optics 40 before entering the fibre 26.

A power laser pulse emitted by the laser 40 is propagated in the central fibre 30 so as to interact with the film 20 and permit the implantation of ions in the area to be treated.

In the case of FIG. 3, the visible light continuously emitted by the laser 38 is inter alia propagated in the annular fibre 32, then in the confinement ring 34 (whose constituent material is transparent to said light) and, when said ring is not in contact with the material 10, said light illuminates the said material and partly returns into the ring 34 and then into the annular fibre.

Observation means 44, e.g. including a video screen, are provided for the observation of the area 18 from said light, which successively reaches them by means of the annular fibre 32, the optics 40 and the optics 42.

As can be seen in FIGS. 2 and 4, it is possible to provide between the optical fibre and the thin film 20, another intermediate thin film 46 constituting an optical impedance matching film. This intermediate film 46 is made from a material making it possible to reduce the optical index jump between the constituent material of the optical fibre 2 or 30, which guides the pulsed power laser beam, and the constituent material of the thin film 20.

The intermediate film 46 makes it possible to reduce the light energy fraction reflected by the fibre/thin film 20 interface and consequently increase the energy density which will be used for explosively evaporating the film 20.

The optical index of the intermediate film 46 is adjusted as a function of the ratio of the optical index of the thin film 20 and the optical index of the core of the optical fibre 2 or 30 transmitting the power laser pulse.

This adaptation of the indices makes it possible to increase the intensity of the shockwave induced by the ionized plasma, increase the surface hardening effect and therefore also the efficiency of the treatment.

The material layer to be implanted in the area to be treated is consumable (being destroyed during the ionic implantation process). This thin film or layer material can be deposited, prior to the use of the apparatus, by a vacuum deposition process such as chemical vapour deposition or plasma vapour deposition.

This deposition can take place directly on the planar face of the optical fibre 2 or 30 intended for transporting the power laser beam.

Figure 5:
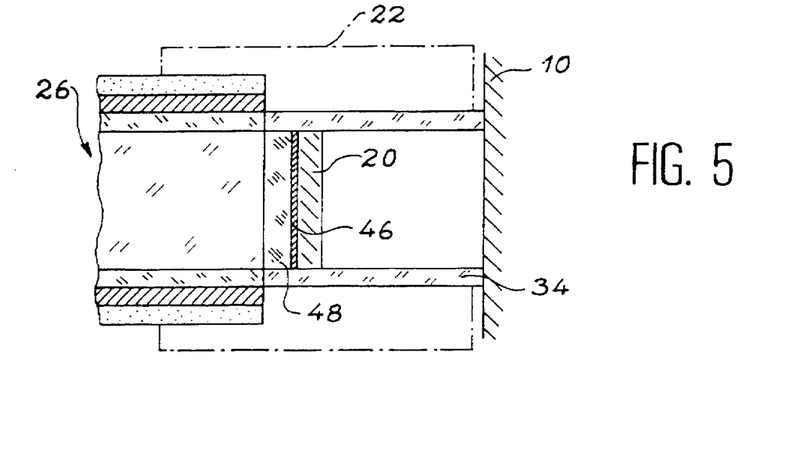
FIG. 5 A diagrammatic view of the photoionic head of an apparatus according to the invention, in which a thin film to be projected on a material is placed on a pellet transparent to the power laser beam used with said apparatus.

As a variant, said film is formed on a pellet 48 (FIG. 5) having a diameter slightly smaller than the internal diameter of the confinement ring and made from a material transparent to the power laser beam, said pellet 48 then being optically coupled to the planar face of the end of the fibre 2 or 30 transporting the power laser beam and as shown in FIG. 5.

Obviously, the intermediate film 46 can be placed between the thin film 20 and the pellet 48.

Then, following each use of the apparatus, it is possible to replace the assembly formed by the confinement ring and the pellet carrying the film 20.

In order to make the apparatus more operational, it is possible to use a not shown drum system provided with several assemblies, each formed by the confinement ring and the pellet 46 carrying the thin film 20, in order to successively bring said assemblies in front of the planar face of the end of the optical fibre intended to transport the power laser pulse.

As a variant, a strip or band is formed carrying the thin film material to be projected and said strip or band is moved between the end of said optical fibre and the confinement ring.

Figure 6:
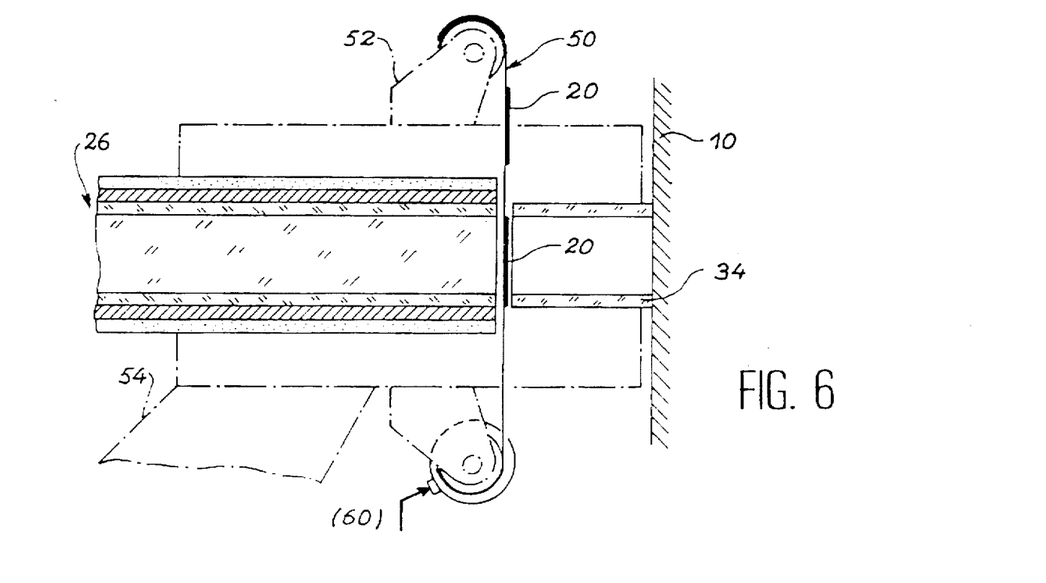
FIG. 6 A partial, diagrammatic view of another apparatus according to the invention usable in continuous manner.

This is more specifically illustrated in FIG. 6, where it is possible to see the strip 50 made from a material transparent to the laser beams used and carrying in its central portion a succession of targets 20 made from the thin film material to be projected, as well as means 52 making it possible to move the strip between the end of the optical fibre intended to transport the power laser beam and the confinement ring, so as to successively bring the targets in front of said fibre.

These means 52 are installed on the part intended to join together the end of the fibre and the confinement ring, as shown in FIG. 6.

Thus, when the thin film material has been projected on an area of the material to be treated, the photoionic head is positioned at another location to be treated of the material and the strip 50 is moved in such a way as to place a new thin film in front of the optical fibre.

Figure 7:
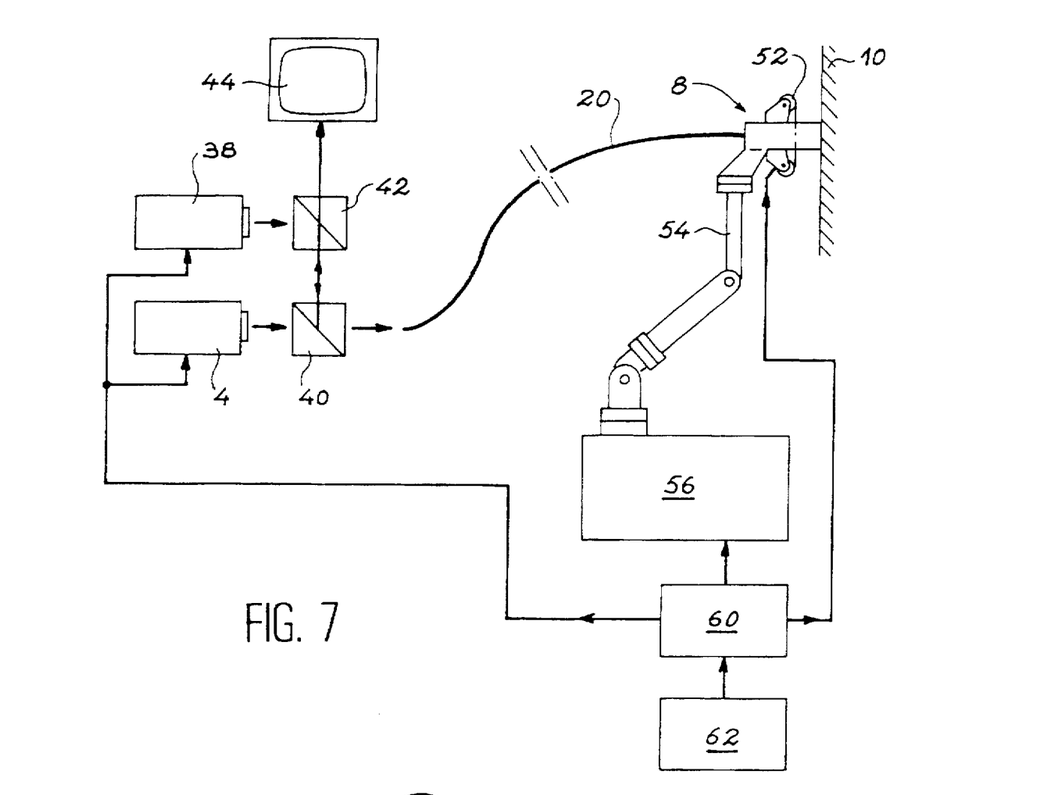
FIG. 7 Diagrammatically the possibility of robotizing an apparatus according to the invention.

FIG. 7 diagrammatically illustrates an apparatus according to the invention comprising means permitting the successive positioning of the photoionic head in areas of the material to be treated which have been determined beforehand.

The apparatus of FIG. 7 comprises a positioning arm 54 joined to the photoionic head 8.

In the embodiment shown, said positioning arm 54 has five axes (three translation axes and two rotation axes) and the arm 54 is controlled by a robot 56 having five axes.

In the embodiment of FIG. 7, the apparatus also comprises means permitting the continuous use thereof, such as e.g. the moving strip system described relative to FIG. 6.

The apparatus of FIG. 7 also comprises a programmable controller 60 for controlling the robot 56, the power laser 4 and the observation laser 38 as well as means 52 permitting the movement of the strip carrying the thin film material to be projected. The programmable controller 60 is controlled by a computer 62 storing a management software for the apparatus. This software manages the different operations of placing the photoionic head 8 at different locations, marked beforehand, of the material 10 to be treated.

It is possible to add to the said apparatus not shown, laser telemetry means making it possible to measure the distance from the photoionic head to the material to be treated.

It is also possible to add to the apparatus of FIG. 7 a not shown camera making it possible to display the complete material or the part to be treated and determine the position of the photoionic head with respect to said part, so as to be able to appropriately position the head facing an area which is to be treated.

Figure 8:
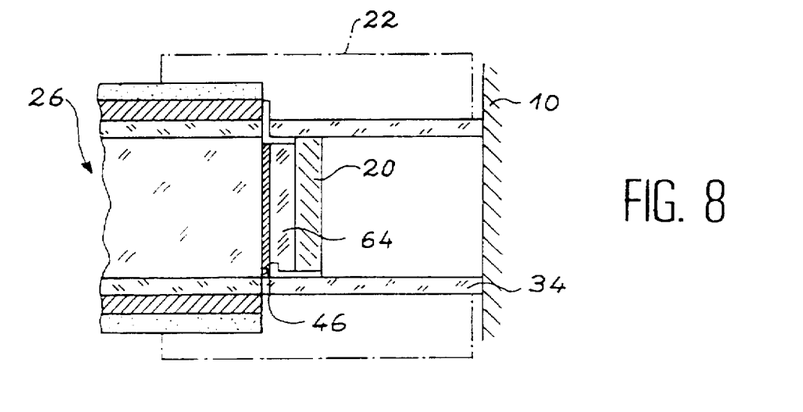
FIG. 8 A diagrammatic view of the photoionic head of another apparatus according to the invention, in which a thin film to be projected on a material is placed on a laser diode.

FIG. 8 partly and diagrammatically illustrates another apparatus according to the invention, in which the photoionic head comprises a diode or laser microchip 64 on which is formed the thin film 20. The terminals of said laser diode 64 are respectively connected to the conductive sheath 12 and to the thin film 20.

As can be seen in FIG. 8, the laser diode 64 is placed against the planar face of the optical fibre for transporting the power laser beam, whilst optionally interposing the intermediate film 46 between said optical fibre and the laser diode (which is placed in the space defined by the confinement ring 16 or 34).

With said laser diode, it is possible to use the power laser 4 for the optical pumping of said laser diode, which is polarized by the polarization means 24 (the target 20 serving as earth).

However, in place of the laser 4, it is possible to use a light source 66 (FIG. 1) able to emit a high intensity, incoherent, pulsed light (e.g. a flash lamp), which also permits the optical pumping of the laser diode 64.

Figure 9:
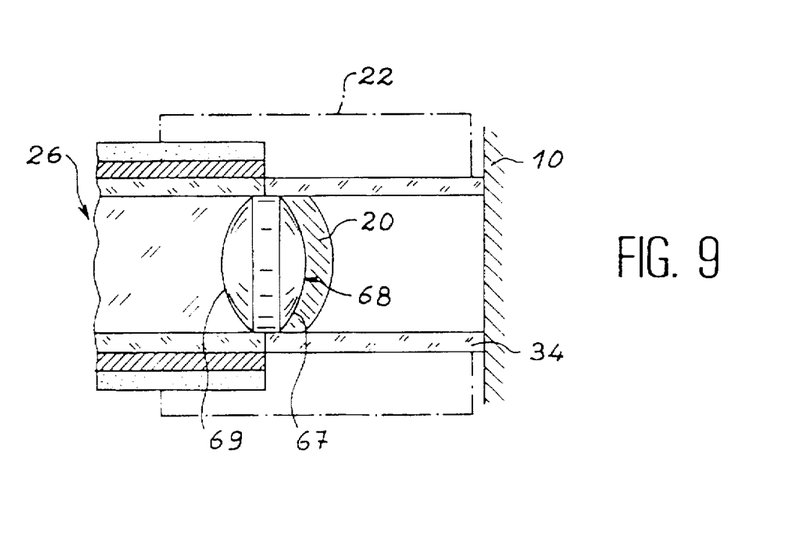
FIG. 9 A diagrammatic view of the photoionic head of another apparatus according to the invention, in which the thin film to be projected is placed on a lens.

FIG. 9 diagrammatically illustrates a variant of the apparatus according to the invention, in which the thin film 20 is formed on a convex face 67 of a convex lens 68, which is optically coupled by its other face 69 to the end of the optical fibre for transporting the pulsed power laser beam.

The lens face 69 can be planar or convex (FIG. 9), in which case the end of the fibre to which it is coupled has a concavity adapted to said face 69.

FIG. 9 shows the convex face 67 carrying the thin film 20 and located in the space defined by the confinement ring, at a distance from the material to be treated, said biconvex lens 68 permitting the focussing onto the thin film of the power laser pulses reaching the same.

Figure 10:
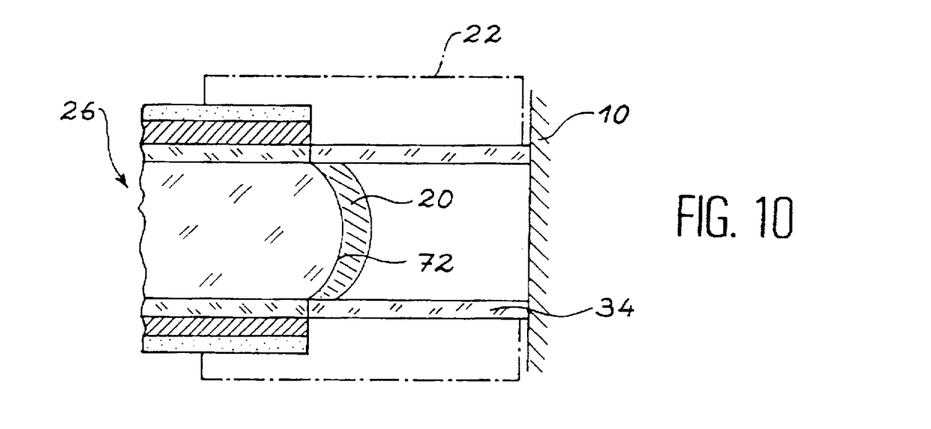
FIG. 10 A diagrammatic view of the photoionic head of another apparatus according to the invention, in which the thin film to be projected is placed on the convex end of an optical fibre.

A variant is illustrated in FIG. 10, where the said lens is eliminated and the optical fibre end 72 for transporting the power laser beam has a convex shape and the thin film 20 is formed on said convex face, said convexity permitting the focussing onto said thin film of the power laser beam.

Figure 11:
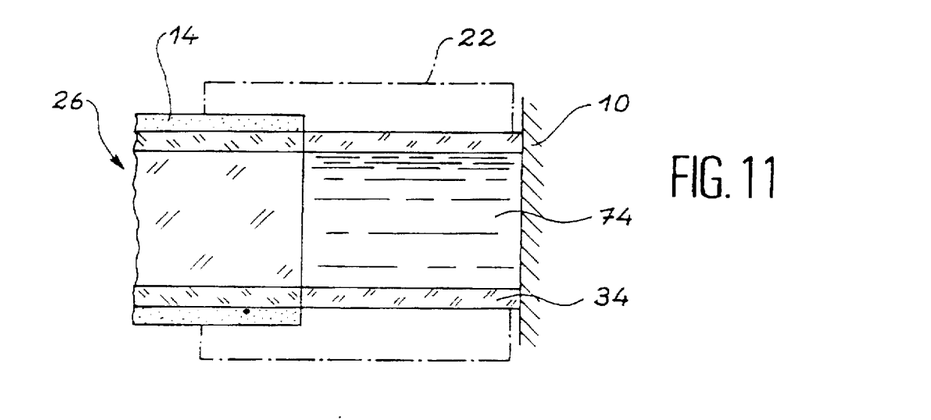
FIG. 11 A diagrammatic view of the photoionic head of another apparatus according to the invention, in which a fluid fills the space defined by a confinement ring with which said apparatus is provided.

FIG. 11 diagrammatically and partially illustrates another apparatus according to the invention, in which the confinement ring is provided with no thin material film to be projected.

The space defined by said confinement ring is filled with a fluid 74 (gas or liquid), which is kept by capillarity in said space (in the case of a liquid), said liquid or gas being transparent to the power laser beam or photodecomposable and photoionizable under the effect of said laser beam.

The apparatus diagrammatically illustrated in FIG. 11 permits the hardening, by surface plasma confinement, of the material to be treated without any supply of substance in the case of a transparent fluid.

In the case where the fluid is photodecomposable and photoionizable, hardening takes place by the chemical species produced during the photoionization and photodecomposition process.

In the case of FIG. 11, the conductive sheath 12 can be eliminated and the protective insulating sheath 14 is then directly in contact with the annular optical fibre 32 (or in an apparatus without means for observing the area to be treated, in contact with the optical fibre 2). In the case of FIG. 11, there is no need to use the polarizing means 24.

Figure 12:
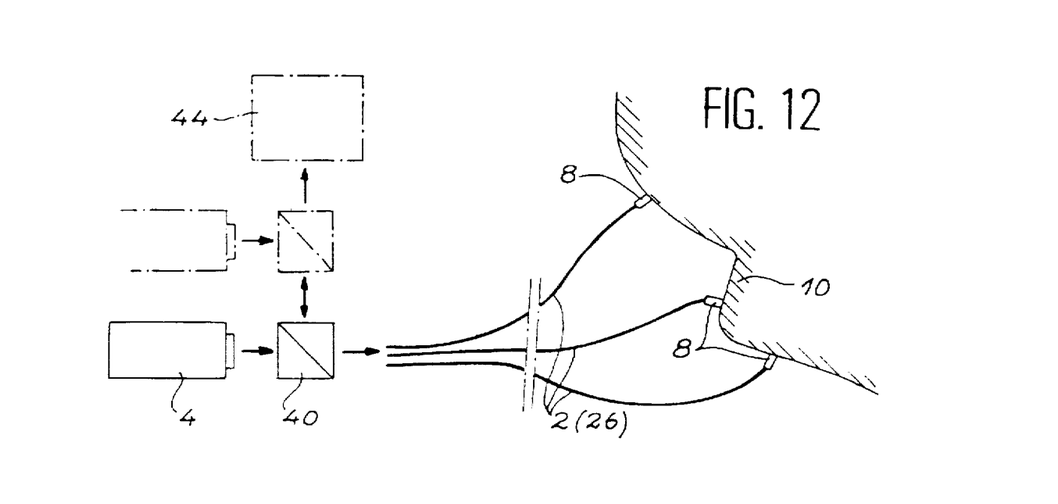
FIG. 12 Diagrammatically an apparatus according to the invention having several photoionic heads.

FIG. 12 illustrates diagrammatically an apparatus according to the invention having a plurality of optical fibres 2 or 26, respectively provided with photoionic heads 8, with a view to simultaneously treating different areas of the part 10 by means of the same power laser 4, whose pulsed beam is simultaneously injected into the different optical fibres.

Obviously it is possible to use a robot for respectively positioning said photoionic heads at the level of the corresponding areas.

It is possible to produce an apparatus according to the invention making it possible to display a part having a random shape on a video monitor, mark the area or areas to be treated, place the photoionic head or heads in said area or areas and treat them. This can, if necessary, be subsequently followed by the treatment of other areas by appropriately moving the photoionic heads and placing new thin films to be projected in said photoionic heads (e.g. with a continuously operating apparatus, in the manner described hereinbefore).

With an apparatus according to the invention, the disadvantage of the known apparatus described in document (2) is eliminated, where it is necessary to spatially correlate the power laser and the laser-assisted ionic implantation cell. In the apparatus according to the invention, the spatial correlation between the power laser and the photoionic head is unnecessary.

In the invention, the assembly incorporating the power laser (or incoherent power source and laser diode), the optical fibre and the photoionic head can easily be rendered compact, sealed and tight to the external atmosphere, e.g. by using a flexible tube in which is formed a vacuum and passage takes place of the optical fibre, by tightly connecting one end of said tube to the laser and the other to the confinement ring. This makes it possible to use an apparatus according to the invention in a radioactive atmosphere, under the sea or even in space.

I claim:

1. Apparatus for the treatment of a material characterized in that it comprises:
   at least one optical fiber (2, 26),
   a first light source (4, 66) for producing a pulsed light permitting the treatment of said material (10),
   a means (6, 40) for injecting said pulsed light into a first end of each optical fiber and
   for each optical fiber, a miniaturized photoionic head (8) whose transverse dimensions only exceed by approximately 20% those of the optical fiber and incorporating a confinement ring (16, 34), whereof a first side of said ring is joined to a second end of the fiber, whereas a second side of the ring is to be placed against said material (10), said ring being able to confine a plasma which can form, due to the pulsed light, in a space (19) defined by said ring, from said material (10) or from a substance (20) placed in said space, for the treatment of said material;
   said apparatus being characterized in that the confinement ring (16, 34) is electrically insulating, each optical fiber (2, 26) being coated with an electrically conductive sheath (12), said substance is placed in the space defined by the confinement ring and forms a solid thin film (20) placed against the second end of the optical fiber and at a distance from said material (10) and which is to be transformed, by means of the pulsed light, into a plasma containing ions; and
   means (24) for polarizing the electrically conductive sheath (12) with respect to said material in order to create, in the space defined by the confinement ring, an electrical field able to accelerate the ions of the plasma towards said material for implanting them therein.

2. Apparatus according to claim 1, characterized in that the substance forming the thin, solid film (20) is electrically conductive or semiconducting.

3. Apparatus according to claim 1, characterized in that the substance forming the thin, solid film (20) is electrically insulating and in that the apparatus also comprises a ring (36), which is electrically conducting and connected to the conductive sheath (12) and which is placed substantially level with the thin film (20), against an outer wall of the confinement ring (16, 34).

4. Apparatus according to claim 3, characterized in that it also comprises a lens (68), which is optically coupled to the second end of the optical fibre and which has a convex face (67) in the space defined by the confinement ring (16, 34), said face is to be located on a side of the material to be treated and in that the thin film (20) is formed on said convex face (67).

5. Apparatus according to claim 3, characterized in that the second end of the optical fibre has a convex portion (72) in the space defined by the confinement ring and in that the thin film (20) is formed on said convex portion (72).

6. Apparatus according to claim 3, characterized in that it also comprises a pellet (48), which is transparent to the pulsed light, which is optically coupled to the second end of the optical fibre (2, 26) and which is placed in the space defined by the confinement ring (16, 34) and whose face which is to be on a side of the material to be treated carries the thin film (20).

7. Apparatus according to claim 3, characterized in that it also comprises a strip (50) on which is formed the thin film (20) and a means (52) for moving said strip between the second end of the optical fibre and the confinement ring.

8. Apparatus according to claim 3, characterized in that it also comprises an intermediate film (46) between the fibre and the thin film (20), said intermediate film serving to adapt the optical index of the fibre to that of the thin film, so as to reduce the pulsed light quantity liable to be reflected by said thin film.

9. Apparatus according to claim 1, characterized in that it also comprises a lens (68), which is optically coupled to the second end of the optical fibre and which has a convex face (67) in the space defined by the confinement ring (16, 34), said face is to be located on a side of the material to be treated and in that the thin film (20) is formed on said convex face (67).

10. Apparatus according to claim 1, characterized in that the second end of the optical fibre has a convex portion (72) in the space defined by the confinement ring and in that the thin film (20) is formed on said convex portion (72).

11. Apparatus according to claim 1, characterized in that it also comprises a pellet (48), which is transparent to the pulsed light, which is optically coupled to the second end of the optical fibre (2, 26) and which is placed in the space defined by the confinement ring (16, 34) and whose face which is to be on a side of the material to be treated carries the thin film (20).

12. Apparatus according to claim 1, characterized in that it also comprises a strip (50) on which is formed the thin film (20) and a means (52) for moving said strip between the second end of the optical fibre and the confinement ring.

13. Apparatus according to claim 1, characterized in that it also comprises an intermediate film (46) between the fibre and the thin film (20), said intermediate film serving to adapt the optical index of the fibre to that of the thin film, so as to reduce the pulsed light quantity liable to be reflected by said thin film.

14. Apparatus according to claim 1, characterized in that the first light source is a pulsed laser (4).

15. Apparatus according to claim 1, characterized in that the first light source is a pulsed, incoherent power light source (66) and in that the apparatus also comprises a laser diode (64) optically coupled to the second end of the optical fibre (2, 26) and able to produce a pulsed power laser beam when it receives pulsed light from the first source (66).

16. Apparatus according to claim 1, characterized in that the optical fibre (26) comprises:

a central optical fibre (30) for transmitting the pulsed light and an annular optical fibre (32) surrounding the central optical fibre, and the apparatus also comprises:

a second light source (38) for producing a visible light permitting the observation of the material (10), a means (42) for injecting said visible light into the annular optical fibre (32) and p1 a means (44) for displaying an image of the material, from the visible light reflected by the material and transmitted by the annular optical fibre (32).

17. Apparatus according to claim 1, characterized in that it also comprises a means (54, 56) for positioning the optical head (8) in front of a chosen area of the material.

18. Apparatus according to claim 1, characterized in that it comprises a plurality of optical fibres (2,26), respectively.

* * * * *